United States Patent [19]

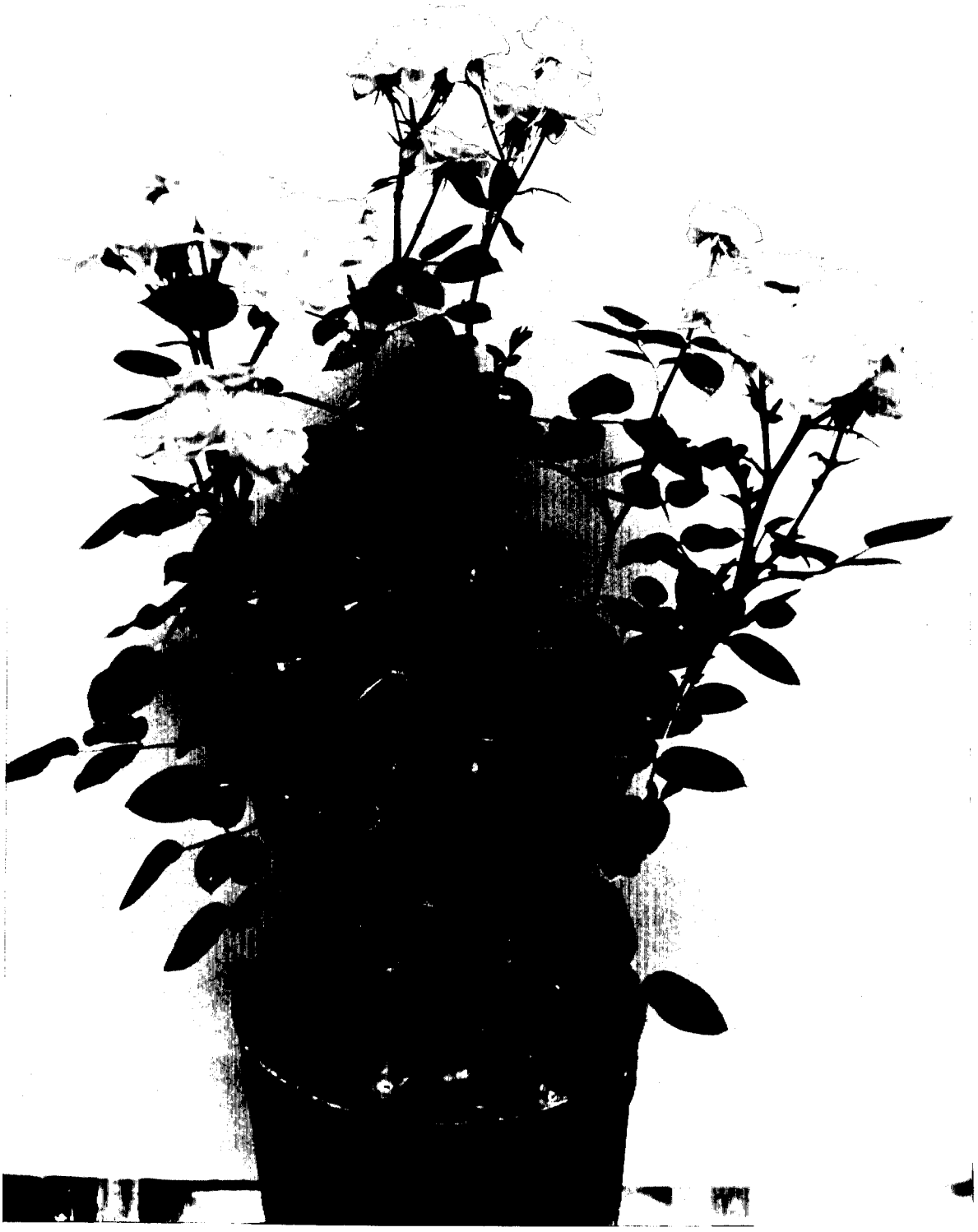

Ilsink

[11] Patent Number: Plant 5,769

[45] Date of Patent: Jul. 22, 1986

[54] ROSE PLANT INTERRO

[75] Inventor: G. Peter Ilsink, Leersum, Netherlands

[73] Assignee: Jackson & Perkins Company, Medford, Oreg.

[21] Appl. No.: 667,126

[22] Filed: Nov. 1, 1984

[51] Int. Cl.[4] ..... A01H 5/00

[52] U.S. Cl. ..... Plt./10

[58] Field of Search ..... Plt./10

*Primary Examiner*—James R. Feyrer

*Attorney, Agent, or Firm*—Manford R. Haxton

[57] ABSTRACT

A miniature rose variety having ability to bloom when very small, easy propagation by cuttings, cherry red blooms borne in clusters, stiff petals and clean foliage.

1 Drawing Figure

This present invention relates to a new and distinct variety of rose plant of the miniature class which was originated by crossing the variety Amanda with an unnamed variety.

The primary objective of this breeding was to produce a new rose variety of the miniature class suitable for use as a flowering pot plant as well as a garden type miniature. This objective was substantially achieved along with other desirable improvements as evidenced by the following unique combination of characteristics which are outstanding in the new variety and which distinguish it from its parents as well as from all other varieties of which I am aware:

1. A dwarf, compact plant capable of blooming when under 6" of height;
2. Easily propagated by cutting;
3. Blooms borne in tight, flat clusters as well as one per stem;
4. Bloom color uniformly light red comparable to Wilson's Cherry 722;
5. Petal count approximately 24 with heavy substance and rigidity; and
6. Good resistance to rose powdery mildew.

Asexual reproduction of this new variety by cuttings, as performed at Irvine, Calif., and Leersum, Holland, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in color illustration of this character.

The following is a detailed description of my new rose cultivar with color in terminology in accordance with the Wilson's Horticultural Colour Chart except where ordinary dictionary significance of color is indicated:

Parentage:
- *Seed parent.*—Amanda.
- *Pollen parent.*—Unnamed variety.

Classification:
- *Botanical.*—Rosa hybrid.
- *Commercial.*—Miniature.

FLOWER

Observations made from specimens grown in a greenhouse at Irvine, Calif. in August.

Blooming habit: Continuous.

Bud:
- *Size.*—$\frac{3}{8}$ to $\frac{1}{2}$" when petals start to unfurl.
- *Color.*—When sepals first divide, Near Cardinal Red 822/3; when half blown, upper side of petals Near Cherry 722; lower side of petals, Near Cherry 722/2.
- *Sepals.*—Color: Scheeles Green 860/3. Three appendaged sepals lightly appendaged. Two appendaged sepals hairy edged.
- *Receptacle.*—Color: Scheeles Green 860/3. Shape: Apple. Size: Relatively large compared to bud. Surface: Slightly pubescent.
- *Peduncle.*—Length: Short. Surface: Glandular with few prickles. Color: Scheeles Green 860/3. Strength: Stiff, erect, slender.
- *Opening.*—Petals fall outward evenly.

Open bloom:
- *Size.*—Small. Average open size $1\frac{3}{8}$".
- *Borne.*—Several together in clusters, flat.
- *Stems.*—Short, strong.
- *Form.*—When first open, flat. Permanence: Retains its form to the end. Petals slightly curled upward.
- *Petalage.*—Number of petals under normal conditions: Approximately 24.
- *Color.*—Center of flower: Upper side of petals, Near Cherry 722; reverse side of petals, Near Cherry 722/2. Base of petals, Near White. Major color: Cherry 722.
- *Variegations.*—Occasional vegetative midrib.
- *Discoloration.*—General tonality at end of third day: Near Cherry 722/1.
- *Fragrance.*—None.

Petals:
- *Texture.*—Thick.
- *Shape.*—Nearly round.
- *Form.*—Edges slightly curled upward.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Large. Color: Yellow, edged orange. Arrangement: Regular around styles.
- *Filaments.*—Color: Base yellow, mostly reddish.
- *Pollen.*—Gold yellow.

*Styles.*—Color: Near White.
*Stigmas.*—Color: Near White.

PLANT

Form: Bush.
Growth: Vigorous, dwarf, upright.
Foliage: Number of leaflets on normal mid-stem leaves: 5, occasionally 7.
*Size.*—Small.
*Quantity.*—Normal.
*Color.*—New foliage: Light green lightly suffused with Garnet Brown 00918/3. Old foliage: Light green.
Leaflets:
*Shape.*—Elliptic.
*Texture.*—Semi-glossy.
*Edge.*—Serrated.
*Serration.*—Single, small.
*Petiole.*—Rachis: Color: Green. Underside: With prickles.
*Stipules.*—Long, bearded.

*Disease resistance.*—Resistant to mildew, under normal growing conditions at Irvine, Calif.
Wood:
*New wood.*—Color: Light green. Bark: Smooth.
*Old wood.*—Color: Green. Bark: Smooth.
Prickles:
*Quantity.*—On main canes from base: Few. On laterals from main canes: Few.
*Form.*—Long, straight.
*Color when young.*—Brown.
Small prickles:
*Quantity.*—On main stalks, none. On laterals, none.

I claim:

1. A new and distinct variety of rose plant of the miniature class, substantially as herein shown and described, characterized particularly as to novelty by the unique combination of its ability to bloom when very small, easy propagation by cuttings, cherry red blooms borne in clusters, stiff petals and clean foliage.

* * * * *